(12) United States Patent
Timmerman

(10) Patent No.: US 8,932,277 B2
(45) Date of Patent: Jan. 13, 2015

(54) INSTRUMENT FOR LAPAROSCOPIC SURGERY

(75) Inventor: Andre Timmerman, Almere (NL)

(73) Assignee: Q Medical International AG, Stein am Rhein (CH)

( * ) Notice: Subject to any disclaimer, the term of this patent is extended or adjusted under 35 U.S.C. 154(b) by 492 days.

(21) Appl. No.: 13/131,822

(22) PCT Filed: Nov. 27, 2009

(86) PCT No.: PCT/EP2009/065996
§ 371 (c)(1),
(2), (4) Date: Jul. 12, 2011

(87) PCT Pub. No.: WO2010/060992
PCT Pub. Date: Jun. 3, 2010

(65) Prior Publication Data
US 2011/0257637 A1    Oct. 20, 2011

(30) Foreign Application Priority Data
Nov. 27, 2008    (DE) .................... 20 2008 015 763 U

(51) Int. Cl.
*A61B 1/00* (2006.01)
*A61B 17/00* (2006.01)
*A61B 17/29* (2006.01)
*A61B 1/005* (2006.01)

(52) U.S. Cl.
CPC ........... *A61B 17/00234* (2013.01); *A61B 17/29* (2013.01); *A61B 1/0056* (2013.01); *A61B 1/005* (2013.01); *A61B 2017/003* (2013.01); *A61B 2017/00407* (2013.01); *A61B 2017/2905* (2013.01); *A61B 2017/2923* (2013.01)
USPC ................ 606/1; 600/141; 600/142; 600/143

(58) Field of Classification Search
USPC ........................................ 600/141–143; 606/1
See application file for complete search history.

(56) References Cited

U.S. PATENT DOCUMENTS

| | | | |
|---|---|---|---|
| 5,522,788 A * | 6/1996 | Kuzmak .......................... | 600/141 |
| 5,618,294 A | 4/1997 | Aust et al. | |
| 5,885,288 A | 3/1999 | Aust et al. | |

(Continued)

FOREIGN PATENT DOCUMENTS

EP    1584293 A1    10/2005

OTHER PUBLICATIONS

International Search Report dated Mar. 17, 2010, in corresponding International Patent Application No. PCT/EP2009/065996, 4 pages.

*Primary Examiner* — Aaron Roane
(74) *Attorney, Agent, or Firm* — Maier & Maier, PLLC

(57) ABSTRACT

In an instrument for laparoscopic surgery, with an operating handle, a rectilinear first shaft section connected to the operating handle, a flexible second shaft section arranged at the distal end of the first shaft section and having an end part located at the distal tip of the second shaft section, wherein the second shaft section can be moved from a rectilinear extension position to a curved position in a predetermined plane of curvature with the aid of a tensioning means engaging on the end part, provision is made for a flexible connecting means to extend between the first shaft section and the end part, and the flexible connecting means has a restoring function with which the flexible second shaft section can be restored automatically to a rectilinear or predetermined extension position.

14 Claims, 4 Drawing Sheets

(56) References Cited

U.S. PATENT DOCUMENTS

Figure 3:
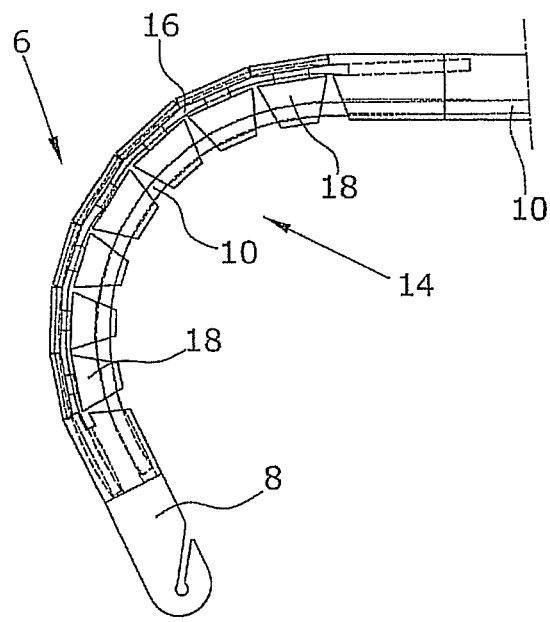

| | | |
|---|---|---|
| 5,919,199 A | 7/1999 | Mers Kelly et al. |
| 5,938,588 A * | 8/1999 | Grabover et al. ............ 600/150 |
| 6,817,974 B2 * | 11/2004 | Cooper et al. ................ 600/142 |
| 7,326,176 B2 * | 2/2008 | Machiya et al. .............. 600/142 |
| 2005/0075538 A1 * | 4/2005 | Banik et al. .................. 600/141 |

* cited by examiner

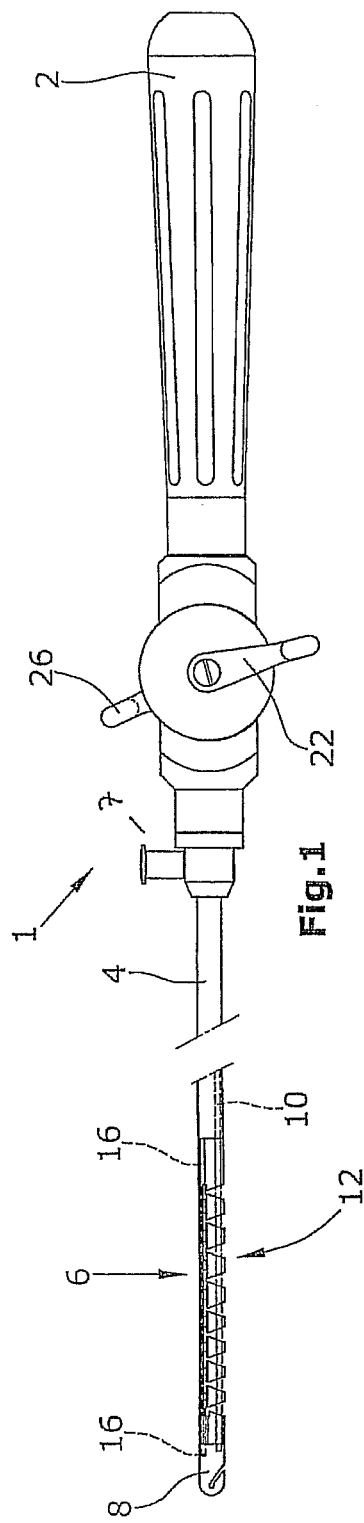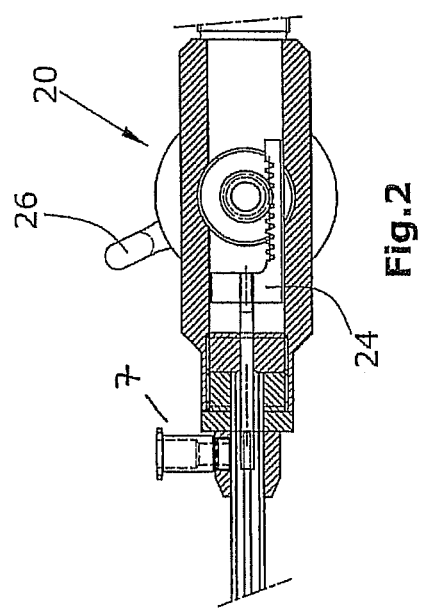

INSTRUMENT FOR LAPAROSCOPIC SURGERY

RELATED APPLICATIONS

This application is the U.S. national stage application which claims priority under 35 U.S.C. §371 to International Patent Application No.: PCT/EP2009/065996, filed on Nov. 27, 2009, which claims priority under 35 U.S.C. §119, to German Patent Application No.: 202008015763.3, filed on Nov. 27, 2008, the disclosures of which are incorporated by reference herein their entireties.

The invention relates to an instrument for laparoscopic surgery according to the preamble of claim 1.

Laparoscopy, also referred to as belly reflection, designates a method by which the abdominal cavity and the organs situated therein are rendered visible by means of special endoscopes, which is performed via a small opening in the abdominal wall that has been created by the surgeon. Via a skin incision, a so-called trocar will be introduced into the abdominal wall, so that the abdominal cavity can be inspected via the trocar with the aid of a laparoscope which is connected to a video camera and a light source.

In a surgical intervention, additional trocars will be inserted via further skin incisions, said trocars allowing laparoscopic instruments to be introduced therethrough into the abdominal cavity, so that the surgical intervention can be performed with the aid of these instruments.

Already known are instruments for laparoscopic surgery which will be introduced, e.g. in rectilinear form, via the trocar into the abdominal cavity and which can perform specific functions within the abdominal cavity.

For this purpose, the instruments comprise an operating handle which makes it possible to perform the functions from outside.

The operating handle first has a rectilinear first shaft section fastened to it. In one of these instruments, it is provided that the first shaft section is followed by a further, flexible shaft section which, with the aid of a tensioning means, is moveable from a rectilinear extension position to a curved position while following a predetermined plane of curvature. Arranged at the distal end of the second shaft section is an end part which optionally has additional functions.

Said end part is connected with two tensile cords which, with the aid of a rotary handle on said operating handle, can be tensioned by shortening the length of the tensile cords so that the flexible shaft section can be bent in a predetermined plane of curvature. The flexible second shaft section comprises individual segments which have abutment faces and thus will delimit the curvature of the second shaft section. When the instrument is to be returned again from its bent end position into its extension position, the rotary handle on the operating handle has to be actuated again, thereby enlarging the length of the tensile cord and allowing the second shaft section to be brought into its extension position again. A disadvantage in this regard resides in that the user will need both hands to operate the instruments. Further, it is disadvantageous that the rigidity of the second shaft section laterally of the plane of curvature will be obtained only when the individual segments have come to rest against their abutment faces.

It is an object of the invention to modify an instrument of the above type to the effect that a single-handed operability is possible and that a higher lateral stability is accomplished also in intermediate positions of the flexible shaft section.

The above object is achieved by the features of claim 1.

The invention advantageously provides that a flexible connecting means extends between the first shaft section and the end part, and that the flexible connecting means has a restoring function with which the flexible second shaft section can be restored automatically to a rectilinear or predetermined extension position.

The single-hand operability makes it possible to introduce the instrument and to simultaneously generate the curvature of the second shaft section in the abdominal cavity by use of a single hand.

Due to the flexible connecting means which comprises a restoring function, the degree of curvature of the flexible shaft section can be changed and adapted to the present requirements at all times without the need of using the second hand for adjusting the curvature. This makes it possible to use the second hand for other activities to be performed in the abdominal cavity with the aid of another instrument. As a result of the flexible connecting means provided in addition to the tensioning means, the second shaft section of the instrument also has a higher lateral stability, i.e. in a direction orthogonal to the plane of curvature of the second shaft section.

Said connecting means can be connected to the first shaft section and the end part in a rigid or a releasable manner. On the distal end of the first shaft section, a coupling means can be provided to allow for exchanging the second shaft section. In this arrangement, said coupling means connects the tensioning means to an operating means on the user's handle, by which the tensioning means can be moved forward and backward. The option of separating the flexible shaft section from the rectilinear first shaft section makes it possible to design the second shaft section as a disposable element, thus facilitating the sterilizing of the instrument.

According to a preferred embodiment, the second shaft section between the first shaft section and the end part is formed by a plurality of individual segments which are moveable relative to each other in an articulated manner.

In this regard, it is provided that said individual segments have a distance from each other and also in the curved end position do not abut against each other by their mutually opposite surfaces.

Said connecting means preferably is a spring element which will automatically return into its originally rectilinear extension position when the tensioning means does not exert a tension on the second shaft section anymore. The spring element can consist e.g. of elastic steel wire.

Preferably, the connecting means is made of a metal with memory effect, e.g. nitinol. Alternatively, the connecting means can contain a metal with memory effect.

Such a memory metal shows a pseudo-elastic behavior wherein the metal, when relieved, will again return to its original shape under the effect of its inner tension.

The connecting means can comprise at least two laterally spaced elements, e.g. wires.

The connecting means can be situated on that side of the individual segments which in the bent state is the outer side.

According to a preferred embodiment, the individual segments comprise base portions, wherein the connecting means is fitted through the base portion of the individual segment.

In this arrangement, the connecting means can be fastened to the end part as well as to the first individual segment.

The tensioning means, in this arrangement, is fitted through these individual segments on that side of the individual segments which is remote from the connecting means.

The maximal displacement path of the tensioning means can be limited by an actuating means in the operating handle. Said actuating means comprises e.g. a pivoting lever on the operating handle which, when the handle is being held, can be operated by a finger.

The maximal displacement path of the tensioning means which determines the degree of curvature of the second shaft section, can be variably adjustable at the actuating means.

Thus, no abutment elements are required on the individual segments.

Preferably, the operating handle is provided with a locking means by which the tensioning means can be locked in selectable tensioning positions. This is to say that, with the aid of the locking means, the flexible second shaft section can be locked into position in each desired curved configuration so that the surgeon can set all intermediate positions between the extension position and the curved end position. Also the locking means is arranged on the operating handle.

The base portions of the individual segments can be arranged adjacent to each other and, when the second shaft section is in a curved state, form a joint. Except for the first and last individual segments, the individual segments are not attached to the connecting means and thus are displaceable on the connecting means.

By way of alternative, the second shaft section, instead of being formed of individual segments, can be made of a flexible solid material or of a flexible tubular material. In such a case, the connecting means can be arranged either externally on said solid material or tubular material, or internally within the solid material or tubular material, while the tensioning means, on the other hand, is in all cases guided within the solid material or tubular material.

For instance, the solid material or tubular material can consist of silicone. In case that the second shaft section is made of a flexible solid material or a flexible tubular material, the connecting means can comprise a thin, flexible strip which will define the plane of curvature in connection with the tensioning means, wherein the restoring force of the connecting means is dimensioned to the effect that also the flexible solid material or the flexible tubular material can be restored to the extension position when the tensioning means does not exert forces anymore.

Embodiments of the invention will be explained in greater detail hereunder with reference to the drawings.

Figure 4:
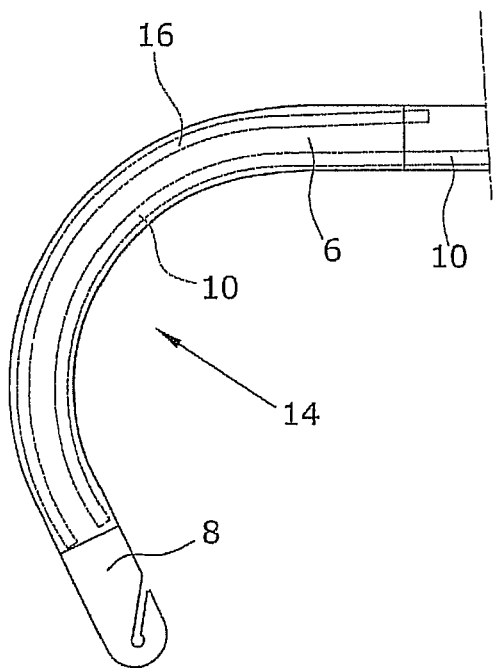
Figure 5:
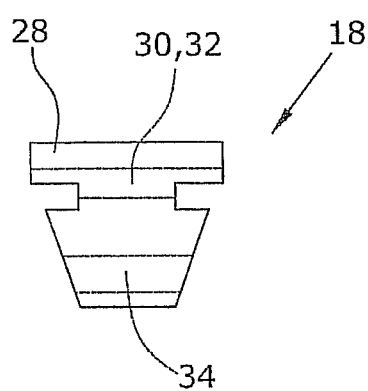
Figure 6:
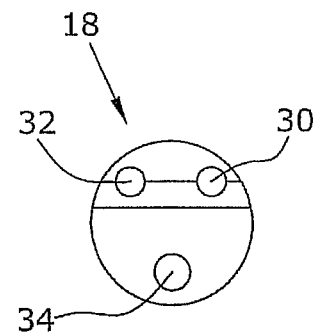

In the drawings,

FIG. 1 is a view of the laparoscopic instrument,

FIG. 2 is a sectional view of the handle in the area of the actuating means, FIG. 3 is a view of a first embodiment of the flexible shaft section, FIG. 4 is a view of a second embodiment of the flexible shaft section, made of elastic plastic material, FIG. 5 is a lateral view of an individual segment of the flexible shaft section, and FIG. 6 is an end view of the individual segment shown in FIG. 5.

Figure 8:
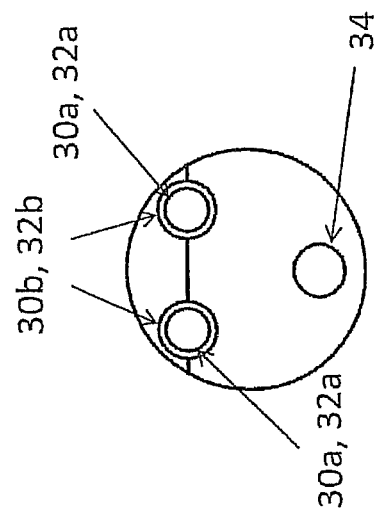
Figure 7:
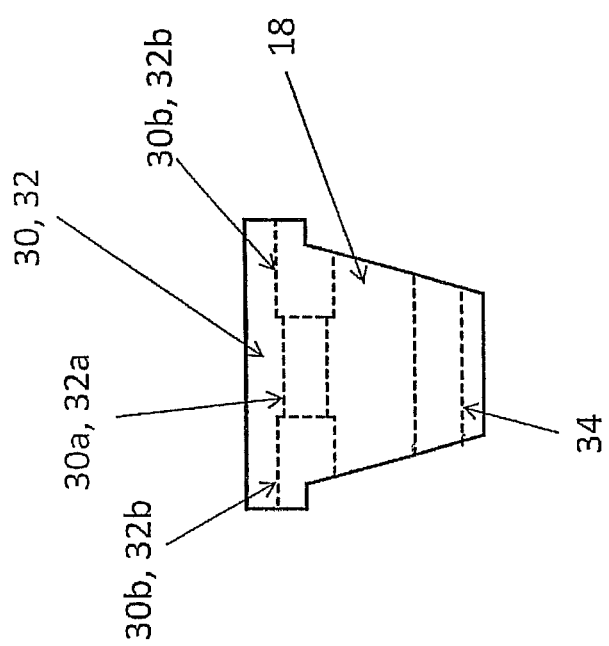

FIG. 7 is a lateral view of an individual segment of the flexible shaft section, and FIG. 8 is an end view of the individual segment shown in FIG. 7

The laparoscopic instrument 1 illustrated in FIG. 1 comprises an operating handle 2, said operating handle 2 being fastened to a rectilinear first shaft section 4. In the distal direction, the distal end of first shaft section 4 is followed by a flexible second shaft section 6 comprising an end part 8 arranged on the tip of second shaft section 6. A tensioning means 10 engages, on the one hand, said end part 8 and, on the other hand, an actuating means 20 comprising a pivot lever 22 and a toothed rack 24 by which said tensioning means 10 can be moved from a rectilinear extension position 12 shown in FIG. 1 into a curved position 14 shown in FIGS. 3 and 4.

Said tensioning means 10, e.g. a tension cord, is coupled to said toothed rack 24. Accordingly, by pivoting said pivot lever 22, the tensioning means 10 can be tensioned whereby the flexible shaft section 6 will be bent, as shown in FIGS. 3 and 4.

Between the first shaft section 4 and the end part 8, a flexible connecting means 16 extends, being fastened to end part 8 and first shaft section 4.

Said flexible connecting means 16 has a restoring function by which the flexible second shaft section 6 can be automatically restored to the rectilinear extension position 12 or a predetermined extension position.

At that end of first shaft section 4 which is facing toward the operating handle 2, a connector 7 for a rinsing solution is arranged. Connector 7 comprises a throughgoing bore. This bore terminates in the hollow first shaft section 4. Via connector 7, the first shaft section 4 and a part of second shaft section 6 can be rinsed. In the process, the rinsing solution will enter the first shaft section 4 via connector 7, rinse the first shaft section 4 and, partially, the channel 34 arranged in second shaft section 6, and will then be discharged at the transition to the first individual segment 18.

In the embodiment shown in FIG. 3, the second shaft section is formed by a plurality of individual segments 18 adapted to be moved relative to each other in an articulated manner.

Said individual segments 18 are arranged at mutual distances.

Also in the curved end position 14, the individual segments 18 are arranged at mutual distances.

FIG. 4 illustrates a second embodiment wherein the second shaft section 6 is made of an elastic material, e.g. silicon, which can be formed as a solid material or a tubular material. In the case of a solid material, the connecting means 16 can be fully enclosed by the silicon material, with the tensioning means 10 being guided within a channel in said solid material.

In the case of a tubular material, the connecting means 16 should be fastened to the inner side or the outer side of the tubular material at least at two sites, while the tensioning means 10 can guided in a freely moveable manner within the tubular material.

FIGS. 5 and 6 illustrate an individual segment 18. From the lateral view shown in FIG. 5, it is evident that the individual segment 18 has a substantially trapezoidal shape which in the plane of curvature of the second shaft section 6 is tapering inward. The individual segment 18 comprises a base portion 28 with two channels 30 and 32, each of said channels having a respective connecting means 16 extending through it. In the trapezoidal portion of individual segment 18, a further channel 34 is provided, having the tensioning means 10 guided therethrough.

The connecting means 16 preferably consists of a metal with memory effect or comprises a metal with memory effect. Such a metal can be e.g. nitinol.

Handle 2, as best seen in FIGS. 1 and 2, is further provided with a locking means 26 for locking the tensioning means 10 in tensioning positions which are selectable at random. As a result, instrument 1 is suited for single-handled operation wherein, with the aid of pivot lever 22, the tensioning means 10 will be actuated and, with the aid of the further pivot lever of locking means 26, pivot lever 22 can be locked in each desired position. The length of the toothed bar 24 will delimit the maximal curvature of second shaft section 6.

According to a preferred embodiment, the second, flexible shaft section 6 is separable from the first shaft section 4, so that the second shaft section is attached to the first shaft section 4 in an exchangeable manner. A coupling means, not shown in the drawings, couples the tensioning means 10 of second shaft section 6 to the operating means.

Since the second shaft section 6 can be designed as a disposable element, it will be, on the whole, easier to sterilize the instrument after each use.

FIGS. 7 and 8 illustrate a further embodiment of the individual segments 18. The individual segments 18 shown in FIGS. 7 and 8 are very similar to the individual segments 18 in FIGS. 5 and 6. The individual segments 18 again comprise two channels 30,32 for respectively one flexible connecting element 16 and one channel 34 for the tensioning means 10.

However, said channels 30,32 for the flexible connecting elements 16 each comprise a first portion 30*a*,32*a* and two further portions 30*b*, 32*b*, wherein the respective first portion 30*a*,32*a* has a smaller diameter than the respective two further portions 30*b*,32*b*. The respective first portion 30*a*, 32*a* is arranged between the respective two second portions 30*b*, 32*b*.

The invention claimed is:

1. An instrument for laparoscopic surgery, comprising
   an operating handle,
   a rectilinear first shaft section connected to the operating handle,
   a flexible second shaft section arranged at the distal end of the first shaft section and having an end part located at the distal tip of the second shaft section,
   the flexible second shaft section being moveable from a rectilinear extension position to a curved position in a predetermined plane of curvature with the aid of a tensioning means engaging on the end part,
   wherein between the rectilinear first shaft section and the end part, the flexible second shaft section is formed by a plurality of individual segments which are moveable relative to each other in an articulated manner,
   wherein
   a flexible connecting means extends between the rectilinear first shaft section and the end part, and
   that the flexible connecting means has a restoring function with which the flexible second shaft section can be restored automatically to a rectilinear or predetermined extension position,
   wherein the individual segments each have a base portion, wherein the base portions of the individual segments butt against each other over the whole width of the segments while forming a joint,
   wherein the flexible connecting means is arranged on that side of the individual segments which in the bent state is the outer side and the tensioning means is fitted through the base portion on that side of the individual segments which is remote from the flexible connecting means.

2. The instrument of claim 1, wherein the flexible connecting means is connected to the rectilinear first shaft section and the end part in a rigid manner.

3. The instrument of claim 1, wherein the individual segments have a mutual distance.

4. The instrument of 1, wherein the individual segments have a mutual distance also in the curved end position.

5. The instrument of claim 1, wherein the flexible connecting means is a spring element.

6. The instrument of claim 1, wherein the flexible connecting means is made of a metal with memory effect, preferably of nitinol, or comprises a metal with memory effect, preferably nitinol.

7. The instrument of claim 1, wherein the flexible connecting means comprises at least two elements which are laterally spaced from each other.

8. The instrument of claim 1, wherein the flexible connecting means is arranged on that side of the individual segments which in the bent state is the outer side.

9. The instrument of claim 1, wherein the individual segment has a base portion arranged thereon and that the flexible connecting means is fitted through the base portion of the individual segment.

10. The instrument of claim 1, wherein the maximal displacement path of the tensioning means is delimited by an operating means in the operating handle.

11. The instrument of claim 1, wherein the maximal displacement path of the tensioning means is variably adjustable at the actuating means.

12. The instrument of claim 1, wherein a locking means is provided for locking the tensioning means in selectable tensioning positions.

13. The instrument of claim 1, wherein the base portions of the individual segments are arranged adjacent to each other while forming a joint.

14. The instrument of claim 1, wherein the flexible second shaft section is exchangeably fastened to the rectilinear first shaft section.

* * * * *